US005676959A

United States Patent [19]

Heitz et al.

[11] Patent Number: 5,676,959

[45] Date of Patent: Oct. 14, 1997

[54] PHOTOTOXIC INSECTICIDAL COMPOSITION AND METHOD FOR CONTROLLING INSECT POPULATIONS

[75] Inventors: James Heitz, Starkville, Miss.; Robert L. Mangan; Daniel S. Moreno, both of Weslaco, Tex.

[73] Assignees: Photodye International, Inc., Linthicum, Md.; The United States of America as represented by the Secretary of the Agriculture, Washington, D.C.

[21] Appl. No.: 543,475

[22] Filed: Oct. 16, 1995

Related U.S. Application Data

[63] Continuation-in-part of Ser. No. 352,925, Dec. 9, 1994, abandoned.

[51] Int. Cl.$^6$ .......................... A01N 25/30; A01N 43/16

[52] U.S. Cl. .......................... 424/405; 424/410; 424/84; 514/455

[58] Field of Search .......................... 424/84, 405, 442, 424/409, 410; 514/455

[56] References Cited

U.S. PATENT DOCUMENTS

| | | | |
|---|---|---|---|
| 4,320,140 | 3/1982 | Crounse et al. | 424/283 |
| 4,647,578 | 3/1987 | Crounse et al. | 514/454 |
| 5,130,136 | 7/1992 | Shono et al. | 424/405 |

*Primary Examiner*—Neil S. Levy

*Attorney, Agent, or Firm*—Bloom & Kreten; The United States of America as represented by the Secretary of Agriculture

[57] ABSTRACT

A phototoxic insecticidal composition includes at least one photoactive dye present in the amount of between 0.025%–4.0% of the composition, an attractant compound and/or feeding stimulant and at least one adjuvant, whereby the adjuvant interacts with the photoactive dye and insect membranes to alter the toxicity of the composition once ingested by the insect.

1 Claim, 2 Drawing Sheets

FIG. I

PHOTOTOXIC INSECTICIDAL COMPOSITION AND METHOD FOR CONTROLLING INSECT POPULATIONS

BACKGROUND OF THE INVENTION

This application is a continuation-in-part application of patent application Ser. No. 08/352,925 filed on Dec. 9, 1994 now abandoned.

FIELD OF THE INVENTION

The present invention relates to insecticidal compositions and, more particularly to an insecticidal composition including a photoactive dye which, when ingested by an insect, becomes phototoxic.

DESCRIPTION OF THE RELATED ART

Many species of insects, from insect groups such as flies, worms, ants, beetles and the like, present a serious threat to agricultural industries throughout the world. In fact, entire harvests have been lost due to insect infestation, costing farmers hundreds of millions of dollars each year. Further, insects of many types present a nuisance and, in some instances, a health risk to humans and many animals. Accordingly, from both an economic standpoint and a health standpoint, it is essential to control the population of certain species of insects from many different insect groups.

For instance, fruit flies of the family Tephritidae include several species that are major pests of agriculture throughout the world and represent a serious threat to U.S. and foreign agricultural industries. The U.S. Department of Agriculture (USDA), Animal and Plant Health Inspection Service (APHIS), in cooperation with other federal and state organizations, has conducted a number of programs to eradicate some species of fruit flies when these insects have been introduced to the U.S. mainland. These programs generally have employed an integrated pest management approach to eradication. Many recent programs have involved application of malathion bait spray to effectively lower fly populations in the infested area, followed by a release of sterile flies. However, aerial applications of the bait spray over populated areas to control infestations of fruit flies have been controversial, and concerns about adverse health effects from exposure to malathion bait spray have been raised by residents of treated neighborhoods.

The currently used malathion bait system, which contains the main ingredients NuLure and malathion for control of mexican fruit flies, uses an attractant (acid hydrolyzed protein) and a contact insecticide (malathion). This system has had a bad public perception. The malathion bait system not only damages paint finishes on cars but also, because of the high concentration of insecticides (10%–20%) in the bait, it has an extremely detrimental effect on other, beneficial insect groups that may contact the bait surface or be exposed to the volatile fumes. The United States government has mandated that certain currently listed pesticides, such as malathion, should have a more restricted use pattern. The Environmental Protection Agency has specifically requested that safer pesticides be developed for use in the agricultural sector.

In the past, xanthene dyes and other photoactive dyes have been used to kill certain species of insects. In particular, the U.S. patent to Crounse, et al., U.S. Pat. No. 4,160.824, discloses the mixture of at least one insecticidally active water soluble xanthene dye and an insecticidally inactive water soluble xanthene dye. Crounse, et al. teaches that the mixture of these dyes is synergistically better than either of the dyes alone.

The addition of a surfactant to a photoactive dye composition is taught by Crounse, et al., U.S. Pat. No. 4,647,578. Crounse, et al. '578 teaches the application of a solid water insoluble dye mixture over an aqueous surface of a mosquito breeding area. The purpose of the surfactant is specifically aimed at a more complete coverage of the dye over the water surface to make it more likely that mosquito larvae will encounter the individual dye particles and mistake them for detritus, the mosquito's normal food, and consume it. Crounse, et al. '578 does not teach that the surfactant enhances the toxicity of the dyes inside the target insect.

The patent to Inazuki, et al., U.S. Pat. No. 4,160,824 teaches the use of a surfactant to emulsify a water insoluble pesticide, such as malathion, so that it becomes soluble in an aqueous medium.

While xanthene dyes have been known to be effective for use in insecticides as evidenced by the patents to Crounse, et al., only a few dyes have been previously found to be effective. Experimental data has shown that the efficacy of these known xanthene dyes, when used alone or in combination with an attractant, is limited and is only effective on certain insects. Further, in many cases, the insect must consume a substantial quantity of the dye composition to reach concentration levels which are sufficient to cause damage and kill the insect.

SUMMARY OF THE INVENTION

Figure 1:
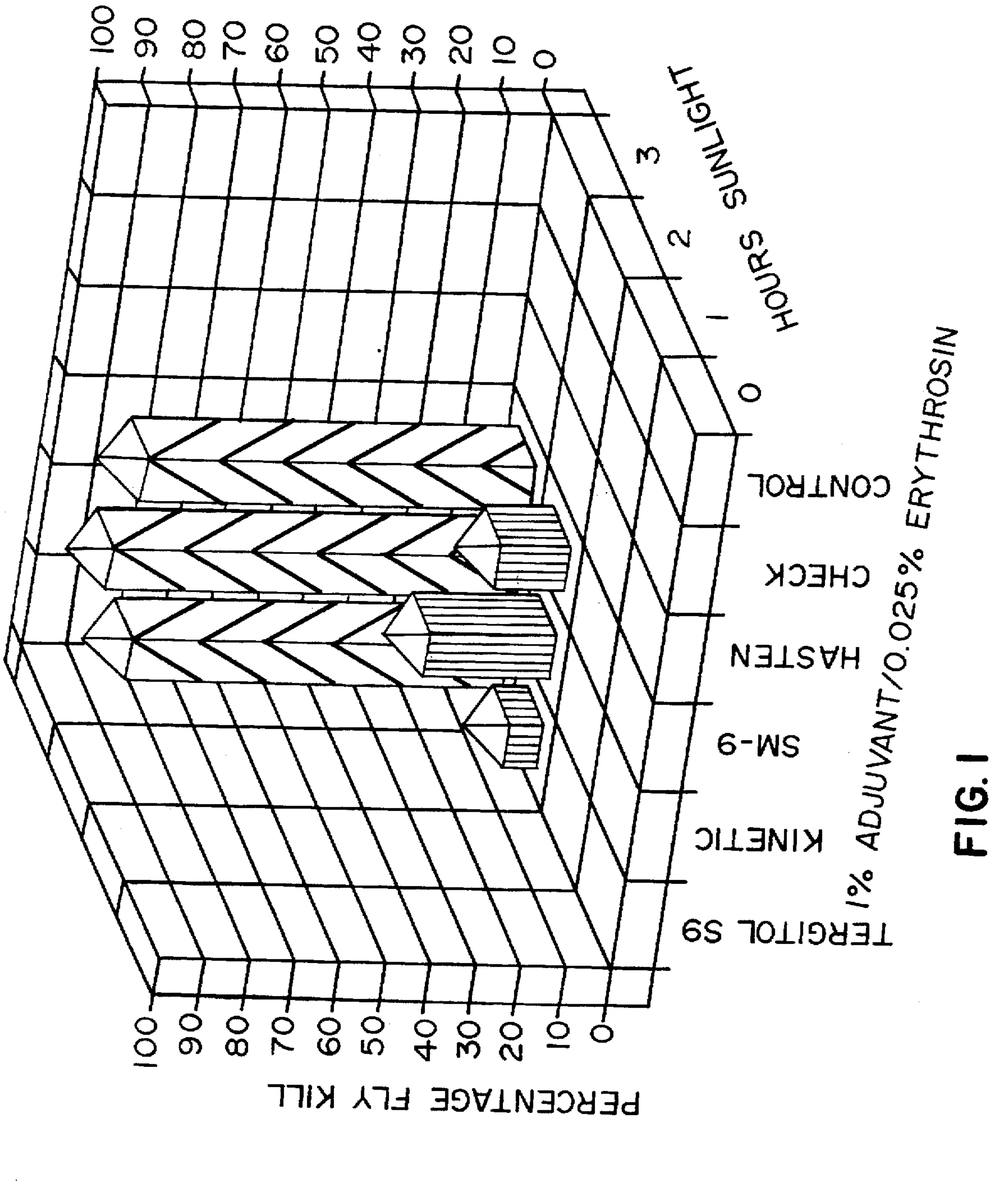
FIGS. 1 and 2 Depict Mortality as a function of Dye and adjuvant.

Through extensive experimental testing and observation, the inventors hereof have determined that a large number of compounds in an array of chemical groups are phototoxic to insects and, the activity of these dyes can be effectively regulated to increase insecticidal efficacy through the use of adjuvants. The efficacy of the observed toxic activity has been unexpectedly shown to be related to a complex interaction between the dye characteristics and the adjuvant chemistry. In a series of tests it was found that without the adjuvants, the majority of the dyes tested had little or no potential as insecticides because they would need to be consumed at concentrations that would inhibit feeding or, they would be excreted from the insect's body before they reached sufficient concentration to damage the insect. The experiments conducted by the inventors hereof have determined that the variation in the killing efficacy (dose and time delay) of the photoactive dyes can be attributed to a much greater extent (and therefore manipulated) by use of particular adjuvants rather than by varying concentrations of the dyes or by interchanging dyes.

The present invention is directed to an insecticidal composition which combines one or more selected photoactive dyes with a selected attractant (bait) and a selected adjuvant, wherein the selected adjuvant interacts with the insect membranes to alter the transport of the dyes through the insect body to susceptible target organs. Accordingly, through specific interactions of the photoactive dye, the selected adjuvant, and the insect membranes, there is a significantly increased, controllable and previously unknown toxic effect that results in mortality of the particular targeted insect.

With the foregoing in mind, it is a primary object of the present invention to provide a phototoxic insecticidal composition comprising at least one photoactive dye, an attractant and/or insect stimulant, and at least one adjuvant selected from a group of adjuvants, wherein the adjuvant alters the toxic activity of the photoactive dye.

It is a further object of the present invention to provide an insecticidal composition comprising at least one photoactive dye, wherein the toxicity of the photoactive dye is controlled for different target insects using one or more selected adjuvants.

It is still a further object of the present invention to provide an insecticidal composition wherein the rate of kill and time of kill of a particular species of an insect group can be controlled and manipulated.

It is yet a further object of the present invention to provide an insecticidal composition comprising at least one photoactive dye and wherein the composition functions inside of a target insect to materially effect the toxicity of the photoactive dye in the insect.

It is yet a further object of the present invention to provide an insecticidal composition which is phototoxic to a specific targeted insect species and yet non-toxic to other insect groups as well as humans, animals and plants.

It is still a further object of the present invention to provide an insecticidal composition which is environmentally safe and which has no detrimental effects beyond the toxic efficacy to a specific targeted insect species.

It is still a further object of the present invention to provide an insecticidal composition comprising at least one photoactive dye and a specific attractant and/or insect stimulant to target a specific species of an insect group so that that particular species will consume the composition.

It is yet a further object of the present invention to provide an insecticidal composition comprising a specific combination of elements including at least one selected photoactive dye, a selected attractant (bait) and/or feeding stimulant to target a specific species of insects and at least one selected adjuvant to control the toxicity of the photoactive dye or dyes once consumed by the target insect, wherein the composition is not attractive to other non-target insects; thereby assuring that beneficial insects will not be harmed or killed by the insecticidal composition.

These and other objects and advantages are more readily apparent in the description and data which follows.

DETAILED DESCRIPTION OF THE PREFERRED EMBODIMENTS

The present invention relates to an insecticidal composition which includes at least one photoactive dye selected from a group of photoactive dyes having a known efficacy when used in the composition for a specific targeted species of insects. The composition further includes at least one attractant compound (bait) and/or an insect feeding stimulant to attract the targeted species of insect so that the targeted insect will consume the composition. Finally, the composition includes at least one adjuvant selected from a group of adjuvants, wherein the selected adjuvant has a known effect in altering the toxicity of the selected photoactive dye once consumed by the targeted insect. Accordingly, use of the selected adjuvant or adjuvants in the composition enables control and manipulation of the time of kill and rate of kill of the targeted insect species.

Through a series of detailed and exhaustive experimental tests, a large number of compounds in an array of chemical groups have been found to have phototoxic effects to specific insects and the toxic activity of these dyes once consumed by the targeted insect has been effectively regulated to control the insecticidal efficacy through the use of selected adjuvants. The following are examples of photoactive dyes which have been found to exhibit phototoxic activity in specific insects when used with one or more selected adjuvants:

Azure A
Azure B
Methylene Blue
NewMethyleneBl N
Toluidine Blue
Methylene Green
Thionin
Brilliant Cresylblue
Rhodamine B
Thioflavine T
Eosine Y
Erythrosine B
Phloxine B
Pyronine Y
Rhodamine 6 G
Rose Bengal
D&C Orange 5
Pyronine B
Neutral Red
Safranin O
Auramine O
Alizarin Red S Included in this list are several dyes which are used as food, cosmetic, or as dyes for cloth, leather, wool, cotton, and the like, which have been approved by the FDA for use as food, drug, or cosmetic. Specifically, the dyes Eosine Y, Erythrosine B, D&C Orange 5, Safranin O. Thioflavine T, and Auramine O were found to exhibit far superior efficacy as insecticides in comparison with Phloxine B, when used with an optimal adjuvant. Without the specific adjuvants, these dyes have little or no toxic activity as insecticides. In fact, Erythrosine B has been cited in scientific literature as being superior to Phloxine B for use as a phototoxic insecticidal dye.

Different embodiments of the composition, comprising at least one of the photoactive dyes, an attractant and/or feeding stimulant, and at least one adjuvant, have been tested on a number of different insect species in different insect groups. The following is a list of insects which have been killed during testing the various embodiments of the composition.

| | |
|---|---|
| Mediterranean Fruit Fly | Boll Weevil |
| Mexican Fruit Fly | Citrus Weevil |
| Oriental Fruit Fly | Soybean Looper |
| Melon Fruit Fly | Diamond Back Moth |
| Malaysian Fruit Fly | Fire Ant |
| Caribbean Fruit Fly | Grasshopper |
| Cabbage Looper | Fern Caterpillar |
| Apple Maggot | Mosquito Larvae |
| Codling Moth | Fall Army Worm |
| Pink Boll Worm | Beet Army Worm |
| Mexican Rice Boll Worm | Colorado Potato Beetle |
| Corn Ear Worm | Cock Roach |
| Tobacco Bud Worm | House Fly |
| Face Fly | Corn Root Worm |

In each of the tests on the above insects, the previously identified photoactive dyes were tested in combination with one or more adjuvants selected from the following group:

| | |
|---|---|
| SM-9 Standard | Tergitol S-9 |
| Dyne-Amic | Solvaid |
| Sylgard | VapoGard |
| Century | Tergitol S-3 |
| Latron B-1956 | Citrufilm |
| Latron CS-7 | Latron AG-98 |
| Tween 20 | Micro |
| Tween 60 | Silwet L-77 |
| Tween 80 | Triton X-100 |
| Hasten | NuFilm 17 |
| Kinetic | NuFilm P |

The chemical makeup or formula for each of the adjuvants that are regarded as most useful in enhancing toxic activity of Phloxine B against Mexican fruit flies are the following:

| Chemical Name | Chemical Components |
|---|---|
| SM-9 | Alkoxypolyethyleneoxyethanol |
| Tergitol | Polyglycol ether |
| Citrufilm | Paraffin base petroleum oil, Polyol fatty acid esters, Poloyoxyethylated polyol fatty acid esters |
| Kinetic | Blend of Polyalkyleneoxide modified Polydimethylsiloxane and non-ionic surfactants |
| Latron AG-98 | Alkyl Aryl Poloxyethylene Glycols |
| Sylgard 309 | 2-(3-hydroxypropyl) Heptamethyltrixiloxane, Ethoxylated acetate, Allyoxy Polyethylene Glycol Monallyl Acetate, Polyethylene Glycol Diacetate |
| Tween 60 | Polyoxyethylene Sorbitan Monostearate |

More specifically SM-9, useful for enhancing the activity of the photoactive dyes is an alkyloxypolyethyleneoxyethanol of the chemical formula $$CH_3-\underset{\displaystyle |\atop \displaystyle O-(CH_2CH_2O)m-H}{CH}(CH_2)n-CH_3$$

wherein n is from 9 to 15 and m is from 3 to 40. The surfactant is disclosed in U.S. Pat. No. 5,026,734.

Tween 60 is a well known ingredient used as an emulsifier and stabilizer in the food industry. It is known chemically as polyoxyethylene-sorbitan monostearate. Tween 60 is more fully described in food Additives Handbook-1989 (editor Lewis) page 359, published by Van Nostrand Reinhold, New York.

The following is a summary of experiments conducted to determine the effect of selected adjuvants on the phototoxicity of certain dyes on the female mexican fruit fly (Anastrepha ludens), house fly larvae in manure piles, and fire ants.

EXPERIMENT 1

In this experiment, the effect of selected adjuvants on the phototoxicity of certain dyes on female mexican fruit flies was determined. The levels of activities of various dye/adjuvant combinations are shown in Table 1a and 1b. The numbers shown in the following tables are percentage of flies killed after 24 hours of feeding and then exposure to sunlight until the most toxic combination in the series reached maximum kill (up to 4 hours). Light intensity was variable among tests, but in the majority of the tests, at least one combination had a greater than 50% mortality.

TABLE 1a

Effect of Selected Adjuvants on the Phototoxicity of Certain Dyes on Female Mexican Fruit Fly, *Anastrepha ludens*

| | % Mortality in the First Spike of Phototoxicity | | | | | |
|---|---|---|---|---|---|---|
| | Phloxine B | | | | | Rose bengal |
| Adjuvants (1%) | 0.0382% | | | | | 0.03% |
| Control | — | — | 2 c | — | — | 0 b |
| Check | 0 b | 0 c | 1 c | 0 b | 4 d | 0 b |
| SM-9 Standard | 2 b | 63 b | 14 b | 70 a | 64 b | 7 b |
| Dyne-Amic | | 28 c | | | | |
| Sylgard | | 94 a | | | | |
| Century | | 67 b | | | | |
| Latron B-1956 | | 5 c | | | | |
| Latron CS-7 | | 2 c | | | | |
| Tween 20 | | | 20 b | | | |
| Tween 60 | | | 31 a | | | |
| Tween 80 | | | 15 b | | | |
| Hasten | | | | 9 b | | 0 b |
| Kinetic | 67 a | | | | | 52 a |
| Tergitol S-9 | | | | 17 b | | 7 b |
| Solvaid | | | | 8 b | | |
| VapoGard | | | | 16 b | | |
| Tergitol S-3 | | | | | | |
| Citrufilm | | | | | 86 a | |
| Latron AG-98 | | | | | 83 a | |
| Micro | 5 b | | | | | |
| Silwet L-77 | 14 b | | | | | |
| Triton X-100 | 4 b | | | | | |
| NuFilm 17 | | | | | 10 d | |
| NuFilm P | | | | | 38 c | |

All adjuvants and dyes were tested in a medium of Mazoferm-Invertose-Water which was fed to flies. Controls contained no adjuvants or dyes; checks contained appropriate dyes but not adjuvants. Means within columns followed by the same letter are not significantly different at p = 0.05 (Fisher's Protected LSD).

TABLE 1b

Effect of Selected Adjuvants on the Phototoxicity of Certain Dyes on Female Mexican Fruit Fly, *Anastrepha ludens*

| | % Mortality in the First Spike of Phototoxicity | | | | | |
|---|---|---|---|---|---|---|
| | Erythrosin | Methylene blue | Azure B | Rhodamine 6G | Thioflavine T | |
| Adjuvants (1%) | 0.025% | 0.0315% | 0.03% | 0.023% | 0.045% | |
| Control | 0 c | 0 d | 3 b | 2 b | 0 d | 0 b |
| Check | 0 c | 91 b | 2 b | 5 b | 0 d | 4 b |
| SM-9 Standard | 24 a | 98 a | 41 a | 18 a | 56 b | 67 a |
| Dyne-Amic | | | | | | |
| Sylgard | | | 43 a | | | 69 a |
| Century | | | | | | |
| Latron B-1956 | | | | | | |
| Latron CS-7 | | | | | | |
| Tween 20 | | | | | | |
| Tween 60 | | | | 4 b | | |
| Tween 80 | | | | | | |
| Hasten | 0 c | 72 c | | | 0 d | |
| Kinetic | 37 a | 96 a | | 10 b | 46 c | |
| Tergitol S-9 | 16 b | 99 a | | | 80 a | |
| Solvaid | | | | | | |
| VapoGard | | | | | | 8 b |
| Tergitol S-3 | | | 42 a | 8 b | | 61 a |
| Citrufilm | | | | | | |
| Latron AG-98 | | | 45 a | | | |
| Micro | | | | | | |
| Silwet L-77 | | | | | | |
| Triton X-100 | | | | | | |

TABLE 1b-continued

Effect of Selected Adjuvants on the Phototoxicity of Certain Dyes on Female Mexican Fruit Fly, *Anastrepha ludens*

| | % Mortality in the First Spike of Phototoxicity | | | | |
|---|---|---|---|---|---|
| | Erythrosin | Methylene blue | Azure B | Rhodamine 6G | Thioflavine T |
| Adjuvants (1%) | 0.025% | 0.0315% | 0.03% | 0.023% | 0.045% |
| NuFilm 17 | | | | | |
| NuFilm P | | | | | |

All adjuvants and dyes were tested in a medium of Mazoferm-Invertose-Water which was fed to flies. Controls contained no adjuvants or dyes; checks contained appropriate dyes but not adjuvants. Means within columns followed by the same letter are not significantly different at $p = 0.05$ (Fisher's Protected LSD).

Table 2 shows a list and the characteristics all dyes tested and having some photodynamic toxicity to fruit flies at less than 0.1% concentration. The majority of these dyes have not previously been reported to have any photodynamic toxicity to insects and several have been tested as set forth in previous publications (without adjuvants) and no toxicity was reported. This experiment has proven that the use of selected adjuvants in combination with at least one photoactive dye results in an internal process in the insect which gives a toxic effect.

lated or only weakly related to the dye solubility in the aqueous bait. Referring to Table 2, methylene blue with a solubility of 50 mg/ml$H_{20}$ has similar 1c 50 . (concentration to kill 50% of test population) to Phloxine B with solubility of 90 mg/ml$H_2O$ and Toluidine Blue at 10 mg/ml$H_2O$.

Different adjuvants had drastically different effects on rate of mortality with the same dye, even in cases with very similar chemical properties of the adjuvants. Tween 60 (Table 1a) was significantly more effective than Tween 80 and NuFilm P was significantly more effective than NuFilm 17 with Phloxine B.

It was observed that the passage of dyes into the hemolymph of the insect was highly dependent on the individual dyes and on individual adjuvants. The appearance of dye in the hemolymph (Table 2) was not observed to be directly related to mortality effects on the insect. Rhodamine B, for example, dyed the body and legs of the insect bright red when used with SM-9 adjuvant, but was only about 30% as toxic to the insect (LC 50=0.09% for Rhodamine B versus 0.030% for Phloxine B). These effects further support our contention that the adjuvants have activity that enhances the photodynamic action of the dyes inside the insects and this activity differs among dyes and adjuvants, but is not due to general solubility mechanisms.

Figure 2:
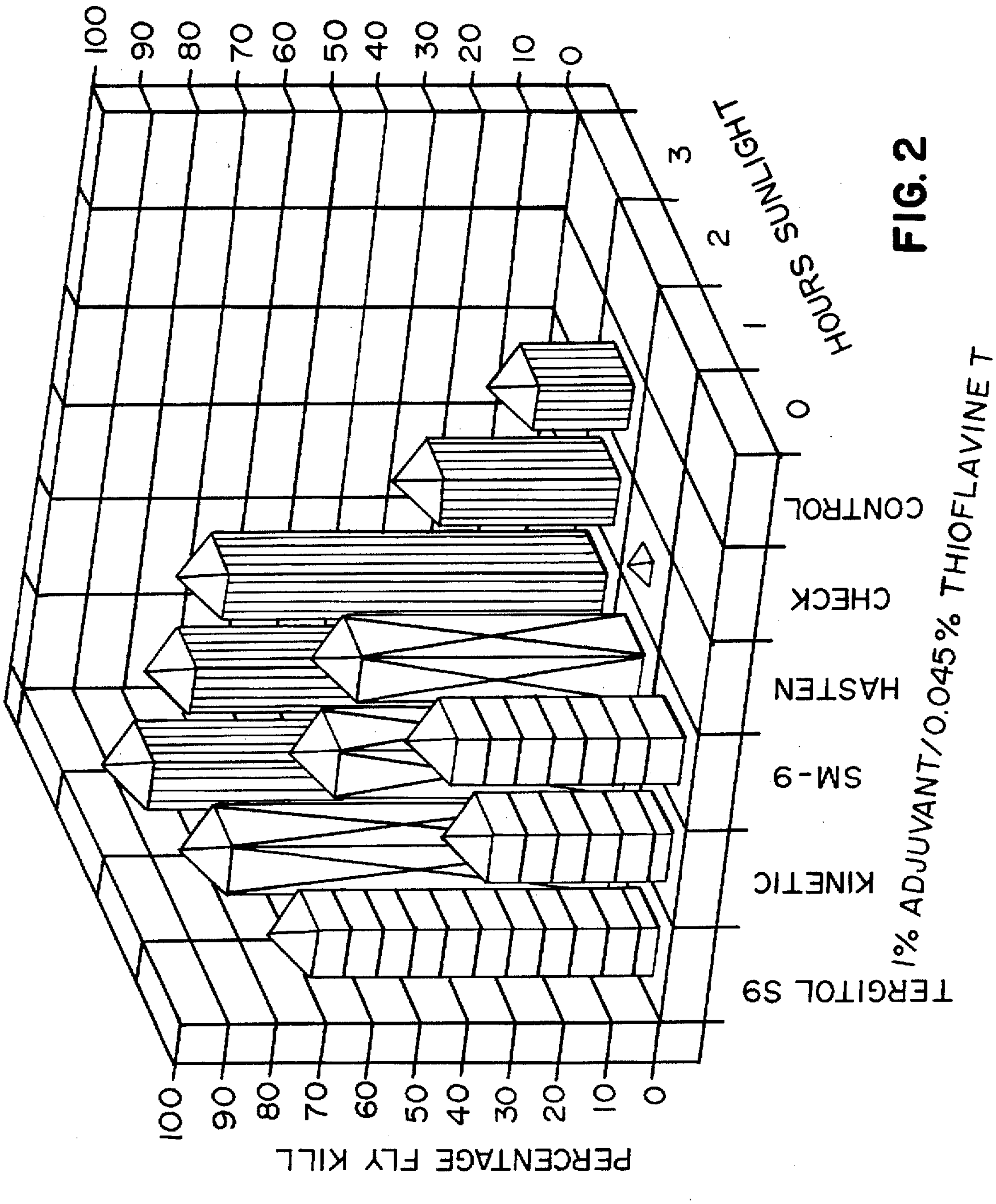

The time delay from exposure to light to the onset of mortality was dependent on an interaction of specific characteristics of the dye and the adjuvant. This is illustrated in FIGS. 1 and 2.

Thioflavine T at 0.045% concentration (the estimated LC 50), with the optimal adjuvant, killed the majority of the flies

TABLE 2

Dyes With Phototoxic Action on the Mexican Fruit Fly, *Anastrepha ludens* Loew[a]

| Dye Name | CI No. | Group/ Sub | Charge | Mol. wt. | Absorb. Max | $LC_{50}$ (%) | Sol. $H_2O$ (mg/ml) | Common Use for Dye |
|---|---|---|---|---|---|---|---|---|
| New MethyleneBl N | 52030 | Thiazine | Cationic | 416.0 | 630 | 0.0174 | 40 | Silk, wool, paper, leather |
| Azure A | 52005 | Thiazine | Cationic | 291.8 | 633 | | 40 | Histology |
| Azure B* | 52010 | Thiazine | Cationic | 305.8 | 648 | | 50 | Histology |
| Methylene blue | 52015 | Thiazine | Cationic | 373.0 | 661 | 0.0315 | 50 | Antiseptic, histology |
| Toluidine blue | 52040 | Thiazine | Cationic | 305.8 | 626 | 0.3004 | 10 | Histology |
| Methylene green* | 52020 | Thiazine | Cationic | 433.0 | 657 | 0.2114 | 30 | Histology |
| Thionin | 52000 | Thiazine | Cationic | 387.3 | 598 | | 30 | Histology |
| Brilliant cresylblue* | 51010 | Oxazine | Cationic | 386.0 | 622 | 0.0389 | — | Histology |
| Rhodamine B | 45170 | Rhodamine | Cationic | 479.0 | 543 | 0.0982 | 30 | Cotton, wool |
| Thioflavine T | 49005 | Thiazole | Cationic | 318.9 | 412 | 0.0303 | 20 | Silk, wool, nylon, acetate |
| Eosine Y | 45380 | Zanthene | Anionic | 691.9 | 514 | | 40 | Histology |
| Erthrosine B | 45430 | Xanthene | Anionic | 879.9 | 525 | 0.0141 | 20 | Food |
| Phloxine B | 45410 | Xanthene | Anionic | 829.7 | 548 | 0.0382 | 90 | Food, cosmetic |
| Pyronine Y | 45005 | Xanthene | Cationic | 302.8 | 548 | 0.2495 | 30 | Histology |
| Rhodamine 6G* | 45160 | Xanthene | Cationic | 479.0 | 524 | 0.0230 | 20 | Printing |
| Rose bengal | 45440 | Xanthene | Anionic | 101.7 | 548 | | 100 | Food, cosmetics |
| D&C Orange 5 | 45370A | Xanthene | Anionic | 490.1 | 450 | | 0.3 | Cosmetics |
| Pyronine B | 45010 | Xanthene | Cationic | 1042.3 | 553 | | 20 | Photography, histology |
| Neutral red | 50040 | Azine | Cationic | 288.8 | 540 | | 40 | Supravital staining |
| Safranin O | 50240 | Azine | Cationic | 350.9 | 530 | 0.0092 | 50 | Cotton, paper, leather |
| Auramine O | 41000 | Diphenyl-methane | Cationic | 303.8 | 432 | | 10 | Cotton, silk, wool, leather |
| Alizarin Red S | 58005 | Anthra-quinone | Anionic | 360.3 | 556 | | 20 | Indicator, histology |

[a]Dyes were fed to flies in a bait formulation of 70% Mazoferm-20% Invertose-1% SM9-Water.
*These dyes colored the whole body of flies, except wings.

For a major portion of the dyes at low concentrations (<0.3%), the check (dye in 8 alone) did not significantly differ in toxicity from the control (bait alone) but the addition of 1% of at least one of the adjuvants resulted in highly significant mortality. The activity of the adjuvants appears to be maximal in enhancing the toxicity at about 1% volume. Enhancing the solubility of the dye in the bait is, however, only a minor function of the adjuvant, as the solubility appears to be maximized at about 0.1% adjuvant by volume. Further, the toxicity of the compounds is unrebefore being exposed to light, but had no effect with Hasten or without the adjuvant until after two hours exposure to light. Erythrosine B at the 0.025% concentration (also the LC 50) caused no mortality with any adjuvant until after two hours exposure to light, but killed most of the insects (and was more effective than Thioflavine T) with the effective adjuvants during the 2–3 hour time period. With no adjuvant, or with Hasten, the Erythrosine B caused no mortality.

The data, in Tables 1a and 1b, comparing check (dye and bait with no adjuvant) and the best adjuvants (dye, bait, adjuvant combination) indicates that greater than 90% mortality can frequently be induced at dye concentrations with adjuvant at the same concentrations that cause no significant mortality in trials without adjuvants.

In addition, the data in Table 3 (below) demonstrates the cumulative mortality rates per hour for a series of concentrations of Phloxine B without adjuvant, and a more than 10-fold decrease in dye concentration with adjuvant. From these observations, it is concluded that the use of adjuvants (1%) allows reduction in dye concentrations by factors of 10 to 50 times of concentration in comparison with formulations without adjuvants. Thus, this experiment has proved the existence of an otherwise unexpected relationship between toxic dyes and a series of adjuvants. The dye and adjuvant combination causes an increased or decreased toxicity depending upon the specific combination of dyes and adjuvants. Further, the increase or decrease of toxicity is not based entirely on solubility considerations of a linear nature.

TABLE 3

Hourly cumulative mortality rates of daylight-exposed Mexican fruit flies that were fed baits with no dye, with 0.038% dye with adjuvant and with increasing concentrations of dye without adjuvants.

| Phloxin B | Percentage Mortality | | | |
|---|---|---|---|---|
| Concentration | 1 hour | 2 hours | 3 hours | 4 hours |
| 0 (control) | 0 | 0 | 0 | 0 |
| 0.038% | 0 | 0 | 0 | 4 |
| 0.25% | 0 | 0 | 2 | 3 |
| 0.5% | 0 | 24 | 53 | 61 |
| 0.038% + SM9 (Adj.) | 4 | 65 | 92 | 98 |

EXPERIMENT 2

This experiment was conducted in order to determine the efficacy of a dye, bait, and adjuvant combination as a phototoxic insecticide for fly larvae. Three different formulas were tested in cow manure piles to determine their toxic efficacy. A first formula contained 4% Phloxine B mixed with deionized water. The second formula contained 3% Phloxine B, 1% Uranine and deionized water. The third formula was comprised of 3% Phloxine B, 1% Uranine, and 2% adjuvant. The kill rate was measured over a period of one week at 2 to 3 day intervals. The kill rate results are shown in Table 4.

TABLE 4

Purpose: Determine the efficacy of photoactive dyes on fly larvae in manure piles
Formula 262-1 Contains 4% phloxine B
Formula 262-2 Contains 3% phloxine B; 1% uranine
Formula 262-3 Contains 3% phloxine B; 1% uranine; 2% adjuvant
The balance of the formula is deionized water
Product applied at the rate of 2 ounces per 100 square feet of manure pile.
Initial Application: 5/18/95
Kill Rate Results:

| Formula | 5/19/95 | 5/21/95 | 5/23/95 | 5/26/95 |
|---|---|---|---|---|
| 262-1 | 10% | 20% | 40% | 60% |
| 262-2 | 10% | 40% | 50% | 80% |
| 262-3 | 20% | 80% | 95% | 95% |

The results of this experiment indicate that the combination of Phloxine B and Uranine produce better and faster kill rates than Phloxine B alone. The addition of the adjuvant accelerates the kill rate, achieving superior results in comparison with Phloxine B alone or Phloxine B with Uranine.

EXPERIMENT 3

This experiment was conducted in order to determine the toxic efficacy of various formulations of a phototoxic composition, with and without an adjuvant, on fire ants.

Three different formulas were tested on fire ants to measure their kill rates. The first formula contained 4% Phloxine B, 1% peanut oil, 1% corn oil, and corn cob grits making up the difference to 100%. The second formula contained 3% Phloxine B, 1% Uranine, 1% peanut oil, 1% corn oil and corn cob grits to 100%. The third formula was comprised of 3% Phloxine B, 1% Uranine, and adjuvant, along with 1% peanut oil, 1% corn oil, and corn grits to make up the difference to 100%. The kill rate was measured over a period of one week at intervals of every two to three days. The kill rate results are shown in Table 5 (below).

TABLE 5

Purpose: Determine the efficacy of various formulations that contain the following combination of active ingredients.
238A — 4% phloxine B
238B — 3% phloxine B; 1% uranine
238C — 3% phloxine B; 1% uranine; 2% adjuvant
The balance of the formulations contains 1% peanut oil, 1% corn oil and corn cob grits making up the difference to 100%.
Initial Application — 8/2/94 Test Site: Bluffton, SC
Product applied at the rate of 1 ounce per 5 square feet of ant hill mound.
Kill Rate Results:

| Formula | 8/3/94 | 8/5/94 | 8/7/94 | 8/10/94 |
|---|---|---|---|---|
| 238A | 10% | 20% | 40% | 60% |
| 238B | 10% | 30% | 60% | 100% |
| 238C | 20% | 80% | 100% | 100% |

The results indicate that the combination of Phloxine B and Uranine exhibit better results than Phloxine B by itself. The addition of the adjuvant greatly enhances the kill rate of the combination of Phloxine B and Uranine.

The present invention contemplates the use of various attractant compounds and/or feeding stimulant compounds. In experiment 1 as set forth above, the adjuvants and dyes were tested in a medium of Mazoferm-Invertose-Water which was fed to the female mexican fruit fly. In experiment 2, cow manure was used as an attractant for fly larvae. In experiment 3, a formulation of peanut oil, corn oil, and corn cob grits was used as an attractant for fire ants. Additional compounds to attract select species of insects, causing them to consume the composition, are set forth in the following Table 6. Any of these compounds can be used in combination with one or more select photoactive dyes and one or more select adjuvants to target a specific species.

In the disclosed invention the photoactive dye is present in the amount of between 0.025% –4.0% by weight of said composition. The adjuvant in the disclosed invention is present in the amount of between 0.25% –3% by weight of said composition.

TABLE 6

Additional Compounds Affecting Insect Behavior

| Compound | Insect: Scientific name | Insect: Common name | Kind of activity | Plant |
|---|---|---|---|---|
| Sinigrin | *Pieris rapae* L. | Imported cabbageworm | Feeding stimulanat | Cruciferae |
| Carvone, methyl chavicol, coriandrol | *Papilo polyxenes asterius* Stoll. | Black swallowtail | Feeding stimulant, attractant | Umbellilferae |
| Guanine, monophosphate | *Musca domestica* L. | Housefly | Feeding stimulant | Yeast |
| Gossypol, quercetin, β-sitosterol, quercetin-7-glucoside, quercetin-3'-glucoside, cyanidin-3-glucoside | *Anthonomus grandis* Boh. | Boll weevil | Feeding stimulant | Cotton |
| Sinigrin, sinalbin, glucocheirolin | *Plutella maculipennis* (Curt) | Diamondback moth | Feeding stimulant | Cruciferae |
| Phaseolunatin, lotaustralin | *Epilachna varlvestis* Mulsant | Mexican bean beetle | Feeding stimulant | Phaseolus |
| Amygdalin | *Malacosoma americana* (Fab.) | Eastern tent caterpillar | Feeding stimulant, attractant | Rosaceae |
| Allyl sulfide | *Hylemia antiqua* (Meig.) | Onion maggot | Feeding stimulant, attractant | Onion |
| Salicin | *Phyllodecia vitallinae* | Willow beetle | Feeding stimulant | Willow var. |
| Cucurbitacins | *Diabrotica undecimpunctata howardi* (Barb.) | Spotted cucumber beetle | Feeding stimulant, attractant | Curcurbitaceae |
| Calotropin | *Poekilocerus bufonius (Klug)* | Grasshopper | Feeding stimulant | Milkweed, *Ascelepius syrica* (L.) |
| 7-α-L-rhamnosyl-6-methoxyluteolin | *Agasicles* sp. (Nov.) | Chrysomelid beetle | Feeding stimulant | Alligatorweed, *Alternathera* phylloxeroides, *Amaranthaceae* |
| p-hydroxyacetophenone,o-hydroxybenzyl aclcohol, p-hydroxybenzyldehyde, (+)-catechin-5-α-D-xylopyranoside, lupeyl oerotate | *Scolytus multristriatus* (*Marsham)* | Smaller European elm bark bettle | Feeding stimulant | Elm, *Ulmus americana* (L.) |
| Anethole, anisic aldehyde | *Papilio polyxenes asterius* (Stoll.) | Black swallowtail | Feeding stimulant | Anise, coriander, celery, angelica, citrus |
| Hypericin | *Calliphora brunsvicensis* | | Feeding stimulant | Hypericum sp. (St. John's wort) |
| Allyl isothiocyanate | *Pieris rapae* L. | Imported cabbageworm | Attractant | Cruciferae |
| 2-hexenol, 3-hexenol, citral, terpinyl acetate, linalyl acetate, linalool | *Bombyx mori* L. | Silkworm | Attractant | Mulberry, *Mortus alba* L. |
| Oryzanone | *Chilo suppressalis* (Walker) | Rice stem borer | Attractant | Rice, *Oryza sativa* L. |
| Coumarin | *Listroderes costirustris oblignus* King | Vegetable weevil | Attractant | Sweet clover, *Melilotus* officinalis L. |
| Amyl salicytate | *Protoparce sexia* (Johan.) | Tobacco hornworm | Attractant | Jimson weed, *Datura* stromonium |
| Methyl eugenol | *Dacus dorsalis* (Hendel.) | Oriental fruit fly | Attractant | Fruits |
| α-Pinene | *Dendroctonus pseudotsugae* (Hopkins) | Douglas-fir beetle | Attractant | Douglas fir, *Pseudorsuga menziezel* Mirb. Franco |
| 1,3 Diolein | *Musca domestica* | House fly | Attractant | Mushroom, *Amarita muscaria* L. |
| Iridodiol, matatabiol, 5-hydroxy-matatabiether, 7-hydroxy-dehydro-matatabiether, allomatatabiol. | *Chrysopa sepiempunctata* (Wesmael) | Lacewings | Attractant | Matatabi, *Actinidia polygama* (Miq.) |
| Benzoic acid, α-terpincol | *Blastophagus piniperda* (L.) | Pine beetle | Attractant | *Pinas densiflora, Pinus* silvestris |
| Ethanol | *Gnatotrichus sulcatus* (LeConte) | Ambrosia beetle | Atttractant | Western hemlock, *Tsuga heterophylla* (R.) Sargent |
| Eugenol, anethole, α-Pinene | *Hylobius pales* (Herbst.) | Pales weevil | Attractant | Loblolly pine stem |
| α-Pinene | *Dendroctonus brevicomis* (LeConte) | Western pine beetle | Attractant | *Pinus ponderosa* (Laws) |
| Syringaldehyde, vanillin | *Scolytus multistriatus* (Marsham) | Smaller European elm bark beetle | Attractant | Decaying hardwood |
| Geraniol, citronellol | *Popilia japonica* | Japanese beetle | Attractant | |
| α-pinene, β-pinene, limonene | *Enoclerus sphegeus* (Fab.) *Enoclerus undatulus* (Say) | Checkered bettle | Attractant | Douglas fir, Ponderosa pine, Grand fir |
| Terpinyl acetate, anethole, terpene alcohols | *Laspeyresia pomonella* L. *Grapholitha (= Laspeyresia)* molesta Busck | Codling moth Oriental fruit | Attractant | |
| Vanillic acid, p-hydroxybenzoic acid, p-coumric acid, protocatechoic acid, ferulic acid | *Kalotermes flavicollis* (Fab.) *Zootermopsis nevadensis* (Hagen) *Heterotermes indicola* (Wasmann) Reticulitermes | Termites | Attractant | Wood infected Basidomycetes |
| β-carotene, niacin, Vitamin $D_1$, cholesterol, diethylstilbesterol, DL-aspartic acid, L-proline, | *Bruchophagus roddi* (Gus.) | Alfalfa seed chalcid | Attractant | Alfalfa |

TABLE 6-continued

Additional Compounds Affecting Insect Behavior

| Compound | Insect: Scientific name | Insect: Common name | Insect: Kind of activity | Plant |
|---|---|---|---|---|
| histidine, pangamic acid | | | | |
| α-Pinene | *Hylotrupes bajulus* (Gyll.) and *H. ater* Payk. (Coleoptera: Scolytidae) | Bark beetles | Attractant | Pinus sp. and others |
| Turpentine, smoke | Cerombycid sp. | Wood boring bettles | Attractant | Wood |
| Geraniol | *Apis mellifera* (L.) | Honey bees | Attractant | General |
| Allyl isiothiocyanate | *Plutella xylostella (Curt)* | Diamondback moth | Oviposition stimulant | *Brassica nigra* L. and other Cruciferae |
| Sinigrin, β-phenyl-ethylamine, allyl isothiocyanate | *Hylema brassicae* (Meigen) | Cabbage maggot | Oviposition stimulant | Swede, *Brassicae napus* L. |
| n-propyldisulfide, methyl disulfide, n-propyl mercaptan, n-propyl alcohol | *Hylema antiqua* (Meigen) | Onion maggot | Oviposition stimulant | Onion |
| α-Pinene, β-Pinene, limonene, eugenol | *Schistocerca gregaria* (Forskal) | A desert locust | Oviposition stimulant | Commiphora |
| Methyl isoeugenol, trans-1,2-dimethoxy-4-propenylbenzene | *Psila rosae* (F:) | Carrot rust fly | Oviposition stimulant | Carrot |

While the instant invention has been described in accordance with what is believed to be preferred and practical embodiments thereof, it is recognized that departures may be made within the spirit and scope of the following claims which are not to be limited except within the doctrine of equivalents.

What is claimed is:

1. A method for killing the Mexican fruit fly comprising applying to the habitat of said Mexican fruit fly a bait composition having enhanced insecticidal activity consisting essentially of effective amounts of a) a phototoxically effective amount of Phloxine B b) an insecticidally enhancing effective amount of an adjuvant of the chemical formula $$CH_3-CH(CH_2)n-CH_3$$
$$|$$
$$O-(CH_2CH_2O)m-H$$

wherein n is from 9 to 15 and m is from 3 to 40 and c) an effective amount of bait containing Mazoferm a) condensed fermented corn extractive), invertose and water.

* * * * *